United States Patent [19]

Vaillancourt

[11] 4,326,569
[45] Apr. 27, 1982

[54] STOPCOCK SEAL

[75] Inventor: Vincent L. Vaillancourt, Livingston, N.J.

[73] Assignee: Critikon, Inc., Tampa, Fla.

[21] Appl. No.: 121,848

[22] Filed: Feb. 15, 1980

[51] Int. Cl.³ ............................................. B65B 3/04
[52] U.S. Cl. .................................... 141/383; 138/89; 285/232
[58] Field of Search ................ 141/27, 329, 330, 383, 141/384, 385, 386; 138/89–95, 96 R, 96 T; 128/239, 247, 218 R; 277/237 R; 285/223, 232

[56] References Cited

U.S. PATENT DOCUMENTS 2,860,820 11/1958 Falligant ............................ 141/383
2,956,737 10/1960 Hager ................................ 141/383

Primary Examiner—Houston S. Bell, Jr.

[57] ABSTRACT

A seal for limiting access of bacteria through a side arm of a stopcock such as that used in apparatus for monitoring pressure in a human blood vessel. The seal has a generally cylindrical body, an open end of which slides over the side arm. A portion of the body seals against the side arm exterior wall. The other end of the seal forms a cap through which a syringe nose may penetrate to establish fluid communication between the syringe and the side arm lumen. The interior of the seal body includes a recess for a Luer lock fitting which may exist on the end of the side arm, and an annular spacer projecting from the inside of the body to provide a surface against which the end of the side arm can abut to prevent the inserted syringe nose from bottoming on the end of the stopcock arm during use. A slit in the capped end of the seal facilitates insertion of the syringe nose. The slit is surrounded by a recess to guide the syringe nose into the slit. The inside of the cap is provided with an additional dome of material to increase the sealing contact between the cap and the syringe nose and so that line pressure in the side arm will help keep the slit closed tight around the end of the syringe nose. A further recess is provided in the seal body adjacent the inside of the cap to receive the material displaced when the syringe nose penetrates the cap.

12 Claims, 4 Drawing Figures

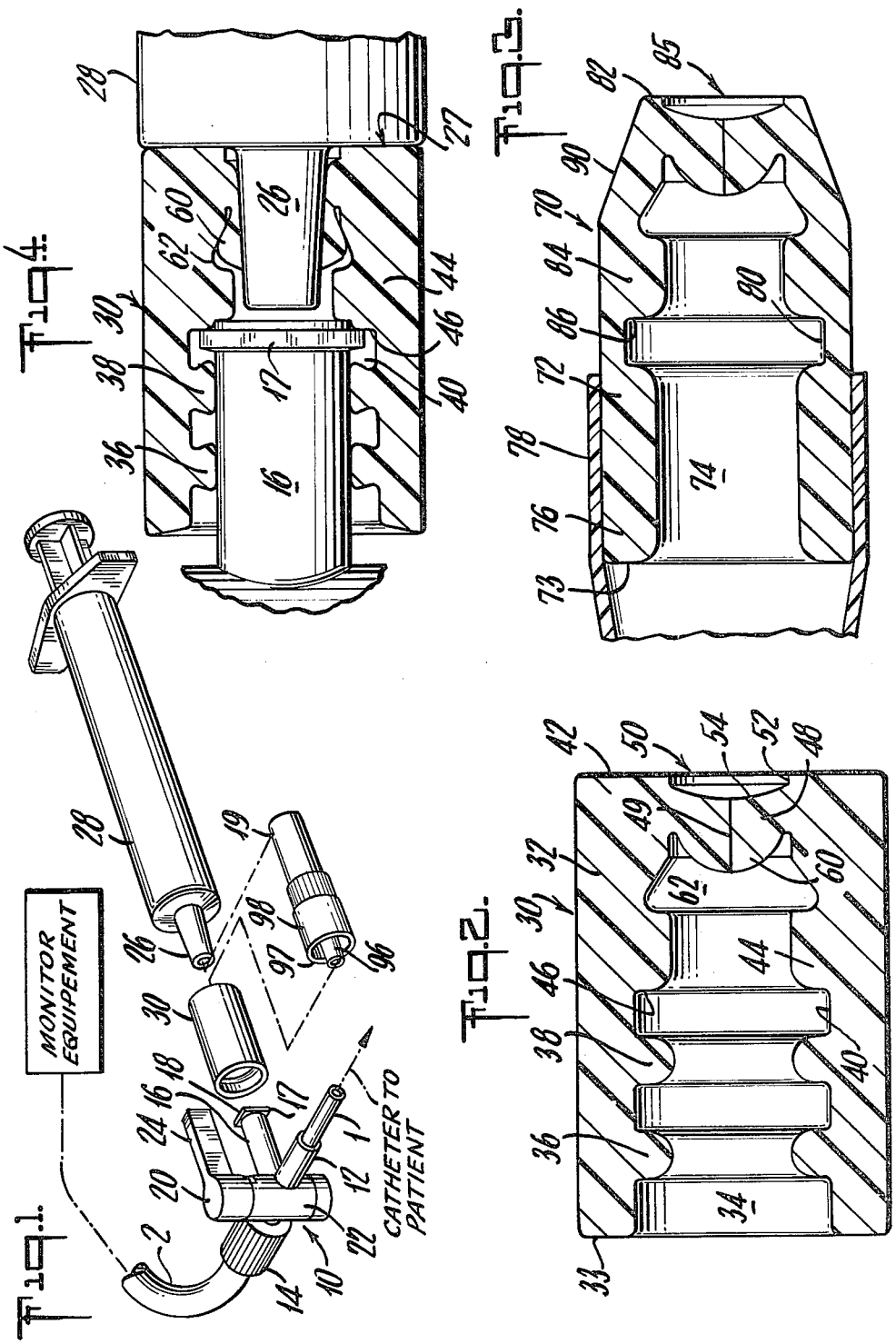

STOPCOCK SEAL

BACKGROUND OF THE INVENTION

The present invention relates to a seal for the side arm of a stopcock of the kind used in apparatus for monitoring pressure in the human blood vessel and, more particularly, to a seal that will permit blood samples to be taken or the line to be flushed through the side arm but which minimizes the access of bacteria to the blood vessel system through the side arm.

In certain medical procedures it is necessary and desirable to monitor the pressure existing in a blood vessel. Part of the system that has been used in the past for accomplishing this blood vessel pressure monitoring is shown schematically in FIG. 1 wherein a first tube 1 is connected to a catheter (not shown) inserted in a patient's blood vessel, and a second tube 2 is connected to monitoring equipment (also not shown). A T-shaped stopcock 10 is connected into the pressure-monitoring line to provide a means for drawing blood, introducing medicament or for otherwise permitting access to the system. Stopcock 10 has a first connection 12 connected to tube 1 and a second connection 14 connected to tube 2 and a side arm 16 with lumen 18 through which access may be gained to the pressure line. Stopcock valve 20 is supported for rotation in an annular housing 22 and may be selectively rotated by means of lever 24 to provide fluid communication between tubes 1 and 2 or between tube 1 and side arm 16. The end of side arm 16 may be fitted with a Luer lock fitting 17 which may include an annular flange extending radially outwardly from the end of side arm 16 or may include one or more tabs (not shown) extending radially outwardly to provide a means onto which female Luer lock fitting 19 may be threaded.

In the past, when it has been desired to take a blood sample the nose 26 of, for example, a blood collection syringe 28 is inserted into lumen 18 of side arm 16 or in the alternative, may be Luer locked onto flange 17 of side arm 16 using Luer lock fitting 19. Stopcock lever 24 is then positioned to permit fluid communication between tube 1 and side arm 16 and to block tube 2. Blood is then drawn and stopcock lever 24 is returned to its original position permitting fluid flow between tubes 1 and 2 and blocking side arm 16. Syringe 28 is then removed.

In the past, side arm lumen 18 and the inside of valve 22 have been open to the atmosphere. After a blood sample has been collected, a certain amount of residual blood may remain coated on the inside surfaces of side arm lumen 18 and on stopcock valve 22. This has provided a site for bacteria growth. The next time blood is drawn from the apparatus and valve 22 is rotated, some of this bacteria may be rotated into fluid communication with tubes 1 and 2 in the main pressure monitoring line and into the main fluid path. This can contaminate the fluid path and can deliver bacteria through the pressure monitoring system to the patient. Since the side arm lumen is often used for the injection of medicament into the patient, any bacteria existing in the lumen or on the valve can be injected directly into the patient along with the medicament. Complications due to secondary infections may result from bacteria ingress through the stopcock mechanism.

The present invention addresses this problem of bacteria ingress through the stopcock mechanism by providing a seal 30 for the stopcock side arm.

SUMMARY OF THE INVENTION

The seal of the present invention is preferably made from a resilient material and includes a body section with a generally axial opening extending into the body for receiving this side arm of the stopcock. The other end of the seal includes a penetrable cap through which the nose of a syringe may be inserted to provide fluid communication between the side arm lumen and the syringe to permit blood samples to be collected or to permit the line to be flushed.

Sealing means are provided between the seal body and the stopcock side arm. In one embodiment of the invention the sealing means include one or more deformable annular rings which deform against the outside surface of the stopcock side arm when the seal is placed over the stopcock. In another embodiment a clearance fit is provided between the inside of the seal body and the side arm, and a shrink band may be placed around the outside of the seal body to provide a tamper proof seal. In still another embodiment an interference fit may be provided and the shrink band may be omitted.

Many stopcock side arms are provided with a Luer lock, i.e., an annular flange extending radially outwardly from the end of the side arm or one or more tabs of various shapes extending radially outwardly from the end of the side arm onto which a Luer lock syringe may be threaded. Thus, a recess is provided within the stopcock body to accommodate the Luer lock fitting. This recess permits the Luer lock fitting to be accommodated without deforming the seal in such a way that might permit contamination from outside bacteria. The seal can be made transluscent in this area to permit the user to visually determine that the Luer lock is properly seated within the recess.

The seal is provided with a spacer which projects from the seal body into the opening a sufficient distance to permit the end of the side arm and the Luer lock, if one is used on the side arm, to abut against the spacer without occluding the side arm lumen. The spacer is used to prevent the end of the side arm from extending too far into the seal so that the nose of the syringe will not bottom on the end of the side arm when the syringe is inserted through the seal cap. The axial length of the spacer is chosen so that a standard syringe with a standard length nose can be inserted all the way into the stopcock seal without hitting the end of the side arm.

The seal cap is provided with a slit to facilitate the insertion of the nose of the syringe. The outside surface of the cap includes a recess about the slit which acts as a guide for insertion of the syringe nose. The inside surface of the cap is provided with additional material to provide additional sealing contact between the cap and the syringe nose. This additional material may be formed into the shape of a generally convex dome projecting into the seal body opening so that line pressure impinging upon the inside of the cap will tend to force the slit closed and minimize leaks. The dome of additional material will also tend to provide tighter sealing engagement between the nose of the syringe and the seal cap.

A further relief recess is provided in the sealed body adjacent the inside of the cap to provide a space for the cap material which may be deformed when the syringe nose penetrates the cap. This permits the syringe nose to be more easily inserted through the cap.

The outside surface of the seal body in the vicinity of the cap may be tapered to accommodate a Luer lock fitting that may be used on the syringe. Thus the syringe nose will be permitted to penetrate the cap before the Luer lock fitting interferes with the outside of the seal body.

The seal is designed to facilitate easy insertion of a syringe and to let the user feel and hear that the syringe has been properly inserted. The recess on the outside surface of the cap surrounding the slit is just slightly larger than the blunt end of the syringe nose. The recess guide in the outside surface of the cap and the relief recess facilitates the easy entry of the nose. However, there is sufficient initial resistance to require a noticeable force for insertion of the syringe. This force reduces noticeably once the nose penetrates the cap and the nose slides in easily until it is stopped by the forward surface of the syringe. The spacer prevents the end of the side arm from extending too far into the seal and spacing the end of the sidearm apart from the end of the syringe nose so that the nose of the syringe does not bottom on the end of the stopcock arm. Thus, the syringe slides in quickly and stops in the right position. The action involved in inserting the nose of the syringe lets the user hear and feel that the syringe is in properly. Thus, users are less apt to have to manipulate the syringe to assure themselves that it has been properly inserted. Such extra manipulation could momentarily open the seal and let bacteria into the seal body or the side arm lumen.

DESCRIPTION OF THE DRAWINGS

These and other features of the invention will be more fully understood from the following detailed description taken in conjunction with the accompanying drawings in which:

FIG. 1 shows an exploded perspective view of the present invention in conjunction with a conventional stopcock and syringe together with an optional Luer lock fitting for the syringe;

FIG. 2 shows a cross sectional view of one embodiment of the seal of the present invention;

FIG. 3 shows a cross sectional view of an alternative embodiment of the seal of the present invention for use with a Luer lock syringe and with the stopcock side arm in place within the seal;

FIG. 4 shows a cross sectional view of the seal shown in FIG. 2 with the syringe and the stopcock in place.

DETAILED DESCRIPTION OF THE DRAWINGS

Referring now to FIG. 1 there is shown a schematic view of the stopcock seal of the present invention generally designated by reference character 30 in conjunction with a stopcock 10 and a syringe 28. The nose 26 of syringe 28 may be fitted with an optional Luer lock fitting 19. The seal 30 fits over side arm 16 of stopcock 10, syringe nose 26, or alternatively the similar nose portion of the optional Luer lock fitting 19 is adapted to penetrate the distal end of seal 30. As will be explained subsequently seal 30 provides a sealing engagement about side arm 16 of stopcock 10 and a sealing engagement about the nose 26 of syringe 28. Thus the ingress of bacteria to stopcock 10, and particularly side arm 16 of stopcock 10, is inhibited by the presence of the seal 30.

Referring now particularly to FIG. 2, there is shown a cross sectional view of one embodiment of the stopcock seal 30. The seal 30 has a generally cylindrical body 32 having a first end 33 adapted for receiving stopcock arm 16 in an opening 34 extending from first end 33 into body 32 in an axial direction. A pair of deformable O-rings 36 and 38 extend from body 32 into axial opening 34 a sufficient distance to provide a seal against side arm 16. As is shown in FIG. 4, O-rings 36 and 38 deform against the outside of stopcock side arm 16 when the seal 30 is inserted over side arm 16 to provide a seal against the atmosphere. An annular recess 40 is provided in seal body 32 to provide a place for housing a Luer lock fitting 17 that may exist on the end of side arm 16. Without recess 40, the Luer lock fitting 17 may have a tendency to deform seal body 32 in such a way that could impair the seal of adjacent O-ring 38 and perhaps even O-ring seal 36. Recess 40 provides a convenient space for the Luer lock fitting 17 and permits the surrounding seal body to remain in its relaxed position, except of course for the O-ring material of O-ring 38 and 36.

As used in this application, the word "cylindrical" is intended to mean a shape generated by moving a line about a path parallel to an axis. It could include a right circular cylinder with a circular cross-section or a variety of other cross-sections including squares, rectangles, ovals or even an irregular shape. The shape of the interior dimension of the seal of the present invention may be modified to accommodate special stopcock side arm shapes.

The body 32 of seal 30 is preferably made in a unitary fashion from a resilient material, such as natural rubber or rubber compositions, or rubber-like synthetic elastomers that possess the compression and rebound of rubber when in the form and shape of the stopcock seal described herein.

O-rings 36 and 38 are preferably formed in a unitary fashion with seal body 32 but alternatively may be separate pieces of rubber or rubber-like material disposed in cooperating annular recesses (not shown) in the seal body which may be made of a different, less resilient material.

Between recess 40 and the second end 42 of seal body 32, there is an annular spacer 44 extending generally radially from the seal body 32 into axial opening 34 a sufficient distance to permit the end of side arm 16 to bottom or spacer 44 without occluding the lumen 18 of side arm 16. Spacer 44 has a surface 46 facing the first end 33 of seal body 32 against which the end of stopcock side arm 16 bottoms.

Spacer 44 is preferably formed in a unitary fashion with seal body 32. However, alternatively it may be a separate piece disposed in a cooperating annular recess (not shown) in seal body 32.

Covering the second end 42 of seal body 32 is a cap portion 48 which blocks the opening 34 extending through seal body 32 from the first end 33. A slit 49 extends generally axially through cap 48 to facilitate the entry of nose 26 of syringe 28 through cap 48, thus rendering the cap penetrable. The material of which cap 48 is made is again resilient-like rubber or a similar compound so that it provides a sealing engagement about the nose 26 of syringe 28 to hinder the ingress of bacteria or the egress of blood fluids through cap 48.

Cap 48 has a recess 50 in its outer surface generally surrounding slit 49 to provide a guide for the entry of nose 26 or syringe 28. Recess 50 should be deep enough to provide a visual and tactile guide for nose 26 but not so deep that it is difficult to clean. As shown in FIG. 2 recess 50 preferably includes a generally axial countersunk portion 52. The outside surface 54 of recess 50 is preferably formed in a concave arc to further facilitate the entry of nose 26 into slit 49.

The inside of cap 48 may include a quantity of additional material 60 which is preferably formed in the shape of convex dome projecting into space 34 from the inside of cap 48 and spaced symetrically about slit 49 through cap 48. This dome of additional material 60 adds additional rigidity to cap 48 so that greater sealing contact is provided about nose 26 of syringe 28 when it is inserted through cap 48. The convex dome shape of this additional material 60 adds to the sealing contact between cap 48 and syringe nose 26 when side arm lumen 18 experiences line pressure. Line pressure in lumen 18 of side arm 16 will be communicated through opening 34 of seal 30 into contact with dome 60, and the pressure will create a force acting on the dome tending to close it tightly about nose 26 of syringe 28. The dome shape of additional material 60 is considered preferable. However, other shapes are considered satisfactory.

A relief recess 62 is provided in seal body 32 adjacent the inside of cap 48, particularly adjacent the additional material 60. Relief recess 62 is preferably symetrically disposed about the axis of seal 30 and preferably tapers radially outwardly in a direction from cap 48 toward first end 33. Relief recess 62 provides a space into which material that may be deformed when syringe nose 26 penetrates cap 48 may migrate. This permits syringe nose 26 to be more easily inserted through cap 48 without binding.

Referring now to FIG. 4, there is shown seal 30 in position over stopcock side arm 16 with nose 26 of syringe 28 inserted through cap 48 into fluid communication with side arm lumen 18. O-rings 36 and 38 are deformed into tight sealing engagement with the outside surface of side arm 16. The end of side arm 16 abuts against surface 46 of spacer 44 to keep side arm 16 from penetrating too far into seal 30. Spacer 44 extends in the axial direction a predetermined distance from surface 46 toward second end 42. This distance is chosen so that the length of the seal, from surface 46 to second end 42, is slightly longer than the length of syringe nose 26, so that when leading surface 27 of syringe 28 bottoms on second surface 42 of seal 30, the end of nose 26 does not touch the end of side arm 16. We have found that for standard blood collection syringes the axial length of spacer 44 is preferably from 0.060 to 0.100 inches and most preferably from 0.065 to 0.070 inches. Since the usual length of nose 26 of the standard blood collection syringe is approximately 0.278 inches, the above specified dimensions for the axial length of spacer 44 provides sufficient additional space for cap 48 and its dome of additional material 60 and relief recess 62. It can be seen that Luer lock fitting 17 fits easily into space 40, provided between O-ring 38 and spacer surface 46, so that the presence of Luer lock fitting 17 does not deform O-ring 38 out of engagement with the outside surface of side arm 16.

Nose 26 of syringe 28 is shown in position with its forward surface 27 abutting against the adjacent surface of seal 30. The dome of additional material 60 is shown displaced into relief recess 62 so that nose 26 may be inserted without substantial binding. The dome shape of additional material 60 is still substantially maintained after the nose has been inserted so that line pressure will tend to force additional material 60 into tight sealing contact around the nose 26. It can also be seen that the end of nose 26 does not bottom on the end of side arm 16.

Referring now to FIG. 3 there is shown an alternative embodiment of the seal of the present invention. The seal 70 of the alternative embodiment has a generally cylindrical body 72 made of a material similar to that of the previously described embodiment. Seal body 72 has a first end 73 adapted for receiving stopcock arm 16 in an opening 74 extending from first end 73 into body 72 in an axial direction toward second end 82. The deformable O-rings 36 and 38 of the first described embodiment are not used with the second embodiment. Instead, seal body 72 extends into opening 74 a sufficient distance to provide a clearance fit between the inside of seal body 72 and the outside surface of side arm 16. A shrink band 78 is then placed about the outside of seal body 72 in a position to overlap side arm 16 and pulled tight and secured to hold and seal stopcock seal 70 onto side arm 16. Shrink band 78 provides a tamperproof seal to prevent stopcock seal 70 from being inadvertently removed from side arm 16. Alternatively, an interference fit may be used and shrink band 78 may be eliminated.

Annular recess 80, similar to annular recess 40 of the first described embodiment, is provided in seal body 72 and provides the same function as recess 40. This second embodiment also includes a spacer 84, similar to spacer 44 of the first embodiment, which also includes a surface 86 against which the end of side arm 16 abuts. Seal 70 also has a cap 85 which is similar in all respects to cap 48 of the first embodiment described above.

Seal 70 of the second embodiment includes a tapered section in the vicinity of cap 85 which tapers radially outward from second end 82 toward first end 73. This taper 90 may be provided on the stopcock seal of either embodiment but is shown here only on the embodiment of FIG. 3 for convenience. The purpose of taper 90 is to permit the seal to accommodate a Luer lock fitting that may be used on a syringe similar to Luer lock fitting 19 shown in FIG. 1. Taper 90 permits the nose 96 of Luer lock adapter 19 to be inserted through cap 85 of seal 70 into its proper position within seal body 72 before the leading edge 97 of Luer lock hood 98 hits against the confronting surface of seal 70. When the syringe nose 96 is inserted properly all the way into seal 70, the forward surface 27 of syringe 28 abuts against the second end 82 of seal 70, and the leading edge 97 of hook 98 of Luer lock adapter 19 just begins to touch tapered surface 90.

Referring again to FIG. 4, the insertion of syringe 28 into stopcock seal 30 will now be described. With stopcock seal 30 securely in place over side arm 16, and the end of side arm 16 resting against surface 46 of spacer 44, the stopcock seal is ready for use. Before syringe 28 is inserted, recess 50 and the surrounding area of second end 42 of stopcock seal 30 is wiped clean with a broad spectrum antibacterial agent. It is particularly important to clean recess 50, including countersunk region 52 and outside surface 54 of the recess. It is important that countersunk region 52 not be too deep so that this area may be quickly and easily cleaned. The kinds of antibacterial agents that may be used are providone iodine, poloxamer iodine or alcohol. Many other kinds of satisfactory agents are known and may be satisfactorily used. The cleaning agent, in addition to cleaning surface 42 of stopcock seal 30, lubricates surface 42 to facilitate the insertion of nose 26 of syringe 28. Cleaning the second surface 42 of seal 30 helps the user identify the location of recess 50 about slit 49 in preparation for insertion of the nose 26 of syringe 28. Nose 26 is then placed against second surface 42 of seal 30 and is easily guided into recess 50 and into slit 49 by concave surface 54. The user then pushes the syringe into slit 49 and feels a noticeable resistance until nose 26 clears the end of slit 49 and enters into space 34 inside seal 30. At this point the resistance to the further insertion of nose 26 is noticeably reduced so that the nose slides easily into the seal until leading surface 27 of syringe 28 abuts against second surface 42 of seal 30. Excess material 60 is partially deformed when nose 26 is inserted and recedes into space 62 so that nose 26 does not tend to bind as it is inserted through cap 48. The end of nose 26 does not bottom on the end of side arm 16 so that syringe 28 does not tend to bounce or catch on the end of side arm 16. Thus, users are less apt to have to manipulate the syringe to assure themselves that it has been properly inserted. Such extra manipulation could momentarily open the seal and let bacteria into the seal body or side arm lumen 18.

Thus, it can be seen that the seal is designed to facilitate easy insertion of the syringe and to let the user feel and hear that the syringe has been properly inserted.

After syringe 28 has been properly inserted into seal 30, valve 20 of stopcock 10 is rotated by means of lever 24 to provide fluid communication between tube 1 and side arm lumen 18 and to block tube 2. Thus, fluid communication is established between syringe 28 and tube 1, which is a catheter leading directly to the patient. After a blood sample has been taken, valve 20 of stopcock 10 is rotated in the other direction by means of lever 24 to provide fluid communication between tubes 1 and 2 and to block side arm lumen 18. Syringe 28 may then be withdrawn from seal 30. As nose 26 of syringe 28 is withdrawn, dome 60 of additional material maintains tight sealing contact with the surface of nose 26 so that blood will not leak from the seal and so that the ingress of bacteria to the seal opening 34 will be minimized. After nose 26 is completely removed, the resilient material of seal 30 returns to its undeformed position to provide a tight seal. Although a quantity of blood may remain within seal 30, the blood is not exposed to the atmosphere so that the chances of bacteria forming in this area are reduced.

It will also be noted that the overall length of the stopcock side arm 16 and seal 30 is small so that it holds only a minimum residual quantity of blood. Any blood which is allowed to remain for an extended period of time within side arm lumen 18 or opening 34 of seal 30 is apt to acquire properties different from that of the patient's blood. Thus, when a second blood sample is taken it is important that this residual quantity of blood, remaining in side arm lumen 18 and opening 34 of seal 30, be small compared to the blood sample taken from the patient so that any change in the properties of the blood remaining inside seal 30 will not affect the overall reading of blood parameters that are obtained when the blood sample is analyzed.

It can be seen that the stopcock seal of the present invention provides an apparatus for limiting the ingress of bacteria to the inside of side arm lumen 18 and valve 22 by sealing these areas to access from the atmosphere. Limiting the growth of bacteria in this area helps eliminate contamination of the pressure monitoring system and correspondingly helps eliminate contamination of the patient's blood stream and resulting secondary infections.

While in the foregoing detailed description there have been described and shown preferred embodiments of the invention, various modifications will be apparent to those skilled in the art to which this invention relates without departing from the scope of this invention. Accordingly, it is not desired to limit the invention except as set forth in the appended claims.

I claim:

1. A seal for a side arm lumen of a stopcock comprising:
    a resilient seal body having a first and a second end and having a channel extending from said first end into said body, said channel being adapted for receiving a stopcock side arm and said first end being adapted for receiving the nose of a syringe; wherein said seal body includes
    (i) sealing means including plural raised lands extending from said body into said channel, thereby defining at least one annular sealing ring for receiving a matable protuberance from the stopcock side arm and adapted for sealing engagement with said stopcock side arm; and
    (ii) penetrable cap means integrally disposed at said second end adapted for permitting penetration by the nose of a syringe therethrough into fluid communication with said opening and providing sealing contact with said syringe, said cap means including a resilient barrier penetrated by a slit, said channel communicating through said second end via said slit, said barrier defining a dome surrounding said slit and extending into said channel, said body defining a radial recess about said dome, whereby the nose of a syringe, when presented at said second end, penetrates said slit, sealably deforming said dome into said recess, and said nose thereby opens into said channel.

2. The apparatus of claim 1 wherein said sealing means includes a plurality of spaced apart annular sealing rings extending from said body into said channel for sealing engagement with said stopcock side arm.

3. The apparatus of claim 1 wherein said sealing means includes a portion of said body extending from said first end into said channel adapted to have a clearance fit with said stopcock side arm.

4. The apparatus of claim 1 wherein said body includes an annular recess between said second end and said sealing means to accommodate a Luer fitting that may exist on the end of said stopcock side arm.

5. The apparatus of claim 5 wherein said body includes a transluscent portion in the vicinity of said annular recess for permitting the user to determine by visual inspection when said Luer fitting enters said recess.

6. The apparatus of claim 1 wherein said second end of said body includes a tapered portion to permit the nose of a syringe which is fitted with a male Luer lock to penetrate said cap means before the hood of said male Luer lock hits on the outside of said seal body.

7. A unitary seal for a side arm lumen of a stopcock comprising;
    a generally cylindrical body having a first end and having an opening extending from said first end into said body, said opening adapted for receiving a stopcock said arm, and said body having a second end adapted to receive the nose of a syringe;
    a plurality of spaced-apart sealing rings extending substantially radially from said body into said opening and adapted to provide sealing engagement with said stopcock side arm by deforming against said stopcock side arm when it is inserted into said opening;

a substantially annular recess in said body disposed adjacent said innermost sealing ring to accommodate a Luer lock fitting that may exist on the end of a stopcock side arm;

a spacer disposed between said annular recess and said second end and extending radially from said body into said opening and having a first surface against which said stopcock side arm bottoms, said spacer extending a predetermined axial distance from said first surface toward said second end, said spacer adapted to prevent said syringe nose from bottoming on said stopcock side arm;

a penetrable cap integrally disposed on said second end and closing said opening, said cap including a slit therethrough for facilitating penetration by the nose of the syringe through said cap into fluid communication with said opening, said resilient material adapted to provide sealing engagement between said cap and said syringe nose;

a recess in the outer surface of said cap about said slit for guiding said syringe into said slit;

an additional quantity of material on the inside surface of said cap disposed as a convex dome projecting into said opening to provide additional sealing contact between said cap and said syringe nose; and, a second recess in said body adjacent said penetrable cap for receiving the cap material displaced when said syringe nose penetrates said cap thereby facilitating easy insertion of said nose into said opening.

8. A unitary seal formed of a resilient material and adapted for sealing the side arm lumen of a stopcock comprising:

a generally cylindrical body having an entrance end and having an opening extending from said entrance end into said body adapted to receive a stopcock side arm, and said body having a capped end adapted for receiving the nose of a syringe;

a seal portion of said body extending from said entrance end into said opening and adapted to provide an interference fit with said stopcock side arm;

a first annular recess disposed in said body inwardly of said seal portion to accommodate a Luer lock fitting that may exist on the end of said stopcock side arm;

a spacer disposed on said body inwardly of said annular recess from said entrance end and projecting into said opening a sufficient distance to permit said stopcock side arm to bottom thereagainst without occluding the stopcock side arm lumen, said spacer extending a predetermined axial distance along said body, said spacer adapted to prevent said syringe nose from bottoming on said stopcock side arm;

a penetrable cap integrally disposed on said second end and enclosing said opening; and, said second end of said body including a tapered portion to permit the nose of the syringe which may be fitted with a male Luer lock to penetrate said cap before the hood of said male Luer lock bottoms on the outside of said seal body.

9. The apparatus of claim 8 wherein said predetermined spacer axial length is a minimum of 0.060 through 0.100 inches.

10. The apparatus of claim 7 further including shrink band means disposed about the periphery of said body in the area of said sealing means for preventing the removal of said seal body from said side arm.

11. The apparatus of claim 1 wherein said sealing means includes a portion of said body extending from said first end into said opening adapted to have an interference fit with said stopcock side arm.

12. The apparatus of claim 3 further including shrink band means disposed about the periphery of said body in the area of said sealing means for preventing the removal of said seal body from said side arm.

* * * * *

UNITED STATES PATENT AND TRADEMARK OFFICE
CERTIFICATE OF CORRECTION

PATENT NO. : 4,326,569
DATED : April 27, 1982
INVENTOR(S) : Vincent L. Vaillancourt It is certified that error appears in the above—identified patent and that said Letters Patent is hereby corrected as shown below:

Column 8, line 50 -"claim 5" should be--claim 4--
Column 8, line 60 -";" should be--:--
Column 8, line 64 -"said" first occurrence should be -- side --.

Signed and Sealed this

Nineteenth Day of October 1982

[SEAL]

Attest:

*Attesting Officer*

GERALD J. MOSSINGHOFF

*Commissioner of Patents and Trademarks*